(12) United States Patent
Azeredo Da Silveira Lajaunias et al.

(10) Patent No.: US 12,427,110 B2
(45) Date of Patent: Sep. 30, 2025

(54) LIPOSOMES FOR INHIBITING BIOFILM FORMATION

(71) Applicant: COMBIOXIN SA, Geneva (CH)

(72) Inventors: Samareh Azeredo Da Silveira Lajaunias, Geneva (CH); Frédéric Lajaunias, Geneva (CH)

(73) Assignee: COMBIOXIN SA, Geneva (CH)

( * ) Notice: Subject to any disclaimer, the term of this patent is extended or adjusted under 35 U.S.C. 154(b) by 613 days.

(21) Appl. No.: 17/172,894

(22) Filed: Feb. 10, 2021

(65) Prior Publication Data

US 2021/0275452 A1 Sep. 9, 2021

Related U.S. Application Data

(63) Continuation of application No. 16/488,516, filed as application No. PCT/EP2018/055061 on Mar. 1, 2018, now abandoned.

(30) Foreign Application Priority Data

Mar. 2, 2017 (EP) ..................... 17158913

(51) Int. Cl.
| | | |
|---|---|---|
| A61K 9/127 | (2025.01) | |
| A61K 31/045 | (2006.01) | |
| A61K 31/685 | (2006.01) | |
| A61K 31/688 | (2006.01) | |
| A61L 2/18 | (2006.01) | |

(52) U.S. Cl.
CPC ............ *A61K 9/127* (2013.01); *A61K 31/045* (2013.01); *A61K 31/685* (2013.01); *A61K 31/688* (2013.01); *A61L 2/18* (2013.01); *A61L 2202/24* (2013.01)

(58) Field of Classification Search
CPC .... A61K 9/127; A61K 31/045; A61K 31/685; A61K 31/688; A61L 2/18; A61L 2202/24; Y02A 50/30; A61P 31/04
See application file for complete search history.

(56) References Cited

U.S. PATENT DOCUMENTS

| | | |
|---|---|---|
| 5,543,152 A | 8/1996 | Webb et al. |
| 5,741,516 A | 4/1998 | Webb et al. |
| 8,906,855 B2 | 12/2014 | Simpkins |
| 9,439,855 B2 | 9/2016 | Simpkins |
| 10,716,756 B2 | 7/2020 | Simpkins |
| 10,744,089 B2 | 8/2020 | Babiychuk et al. |
| 2003/0175334 A1 | 9/2003 | Bolton et al. |
| 2007/0122466 A1 | 5/2007 | Chancellor et al. |
| 2013/0089598 A1* | 4/2013 | Gupta .............. A61K 31/375 424/450 |
| 2015/0157570 A1 | 6/2015 | Babiychuk et al. |
| 2015/0259382 A1* | 9/2015 | Wang .............. A61K 45/06 514/2.7 |

FOREIGN PATENT DOCUMENTS

| | | | |
|---|---|---|---|
| CA | 2 703 179 | * | 4/2009 |
| JP | 2015-519383 A | | 7/2015 |
| WO | 2013/186286 A1 | | 12/2013 |
| WO | 2017/222912 A1 | | 12/2017 |

OTHER PUBLICATIONS

Dong, D et al in PLOS One, vol. 10, 1-16 and Jun. 2015.*
Furukawa_et_al, Journal of Bacteriology, Feb. 2006, pp. 1211-1217.
Lee_et_al, Journal of Microbiol. Biotechnol, 2017, 27(6), pp. 1053-1064.
Roy et al., Virulence, 2018, vol. 9, No. 1, pp. 522-554.
Valentini et al, ScienceDirect, Current Opinion in Microbiology, 2018, 41:15-20.
International Search Report issued in International Application No. PCT/EP2018/055061, dated May 8, 2018.
Bhattacharya et al., "Prevention and treatment of Staphylococcus aureus biofilms," Expert Rev Anti Infect Ther. 13(12):1499-1516 (2015).
Dong et al., "Distribution and Inhibition of Liposomes on *Staphylococcus aureus* and *Pseudomonas aeruginosa* Biofilm," PLOS One 10(6):1-16 (2015).

(Continued)

*Primary Examiner* — Walter E Webb
(74) *Attorney, Agent, or Firm* — BakerHostetler

(57) ABSTRACT

The present invention relates to a composition comprising, preferably consisting of, (i) a single empty liposome, wherein said single empty liposome is selected from (a) an empty liposome comprising cholesterol, wherein the amount of cholesterol is at least 30% (weight per weight), wherein preferably said empty liposome comprising, further preferably consisting of, cholesterol and sphingomyelin; or (b) an empty liposome consisting of sphingomyelin; or (ii) a mixture of empty liposomes; wherein said mixture of empty liposomes comprises, preferably consists of, at least one empty liposome selected from (a) an empty liposome comprising cholesterol, wherein the amount of cholesterol is at least 30% (weight per weight), wherein preferably said empty liposome comprising, further preferably consisting of, cholesterol and sphingomyelin; (b) an empty liposome consisting of sphingomyelin; and (c) an empty liposome comprising, preferably consisting of, phosphatidylcholine and sphingomyelin; and at least one empty liposome independently of each other selected from an empty liposome comprising, preferably consisting of, lipids or phospholipids selected from cholesterol, sphingomyelins, ceramides, phosphatidylcholines, phosphatidylethanolamines, phosphatidylserines, diacylglycerols, and phosphatidic acids containing one or two or more saturated or unsaturated fatty acids longer than 4 carbon atoms and up to 28 carbon atoms; for use in a method for preventing or reducing biofilm formation or for eradicating or reducing existing biofilm.

7 Claims, 1 Drawing Sheet

(56) References Cited

OTHER PUBLICATIONS

Henry et al., "Engineering liposomes sequester bacterial exotoxins and protect from severe invasive infections in mice," Nature Biotechnology 33(1):81-91 (2015).
Azeredo Da Silveira et al., "Liposomes as novel anti-infectives targeting bacterial virulence factors?", Expert Review of Anti-Infective Therapy, 2015, vol. 13, No. 5, pp. 531-533.
Bjarnsholt et al., "Applying insights from biofilm biology to drug development—can a new approach be developed?", Nat. Rev. Drug Discov., 2013, vol. 12, pp. 791-808.
Braun et al., "Pneumolysin, a Protein Toxin of Streptococcus pneumoniae, Induces Nitric Oxide Production from Macrophages", Nfection and Immunity, vol. 67, No. 8, Aug. 1999, pp. 3750-3756.
Cai et al., "Novel Insights for Systemic Inflammation in Sepsis and Hemorrhage", Mediators of Inflammation, vol. 2010, Article ID 642462, pp. 1-10.
Davies, "Understanding Biofilm Resistance to Antibacterial Agents", Nat. Rev. Drug Discov., 2003, vol. 2, pp. 114-122.
Francois et al., "CAL02: a liposomal adjunctive anti-toxin therapy in infections. A new therapeutic approach for severe community-acquired pneumonia", PowerPoint from the European Congress of Clinical Microbiology and Infectious Diseases, Apr. 22-25, 2017, pp. 1-18.
Hammond et al., "Balanced Crystalloids versus Saline in Critically Ill Adults—A Systematic Review with Meta-Analysis", NEJM Evid, vol. 1, No. 2, Jan. 18, 2022, pp. 1-12.
Henry et al., "Engineered liposomes sequester bacterial exotoxins and protect from severe invasive infections in mice," Nature Biotechnology, 2014, vol. 33, No. 1, pp. 81-88.
Laterre et al., "CAL02, a novel antitoxin liposomal agent, in severe pneumococcal pneumonia: a first-in-human, double-blind, placebo-controlled, randomized trial," Lancet Infect Dis, May 2019, vol. 19, pp. 620-630.
Lee et al., "The Hypotension Period after Initiation of Appropriate Antimicrobial Administration Is Crucial for Survival of Bacteremia Patients Initially Experiencing Severe Sepsis and Septic Shock", J. Clin. Med., Aug. 12, 2020, vol. 9, pp. 2617-2629.
Peneysan et al., "Antibiotic Discovery: Combatting Bacterial Resistance in Cells and in Biofilm Communities", Molecules, 2015, vol. 20, pp. 5286-5298.
Qu et al., "Case report of rescue of a patient with COVID-19 and shock after holmium laser lithotripsy", Int J Urol Nurs., 2022, vol. 16, No. 03, pp. 245-251.
Rabin et al., "Biofilm formation mechanisms and targets for developing antibiofilm agents", Future Med. Chem., 2015, vol. 7 No. 4, pp. 493-512.
Rasamiravaka et al., "The Formation of Biofilms by Pseudomonas aeruginosa: A Review of the Natural and Synthetic Compounds Interfering with Control Mechanisms", BioMed Research International, vol. 2015, pp. 1-17.
Tracey et al., "Anti-cachectin/TNF monoclonal antibodies prevent septic shock during lethal bacteraemia", Nature, vol. 330, No. 6149, Dec. 17, 1987, pp. 662-664.
Tran et al., "The Pseudomonas aeruginosa Type III Translocon Is Required for Biofilm Formation at the Epithelial Barrier", PLOS Pathogens, 2014, vol. 10 No. 11, pp. 1-11.
Weinberg et al., "Interleukin-1 and tumour necrosis factor cause hypotension in the conscious rabbit", Clinical Science, Feb. 16, 1988, vol. 75, No. 3, pp. 251-255.
Wu et al., "Strategies for combating bacterial biofilm infections", International Journal of Oral Science, 2015, vol. 7, pp. 1-7.
Xu et al., "Noma in a boy with septic shock: a case report", BMC Pediatrics, 2019, vol. 19, 200, pp. 1-5.

* cited by examiner

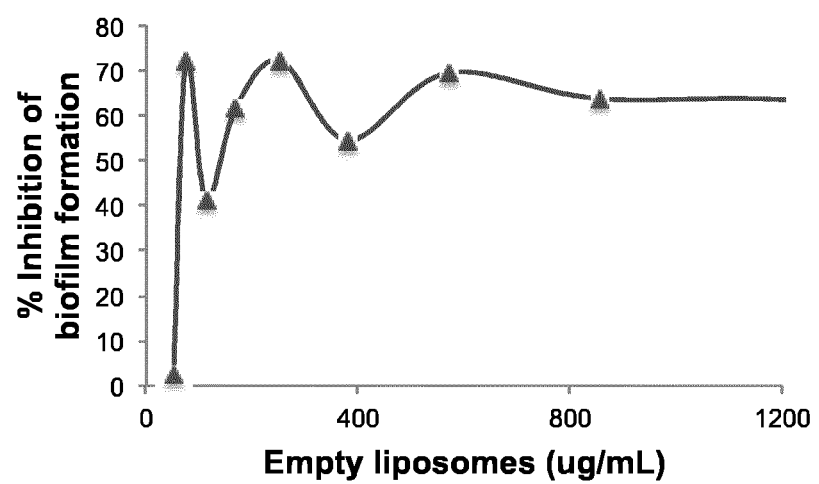

LIPOSOMES FOR INHIBITING BIOFILM FORMATION

The present invention relates to empty liposomes or mixtures of empty liposomes of defined lipid composition for preventing or reducing biofilm formation or for eradicating or reducing existing biofilm. The present invention further relates to a treatment or prophylaxis of such biofilm formation by using the inventive empty liposomes or mixtures of empty liposomes, alone or in combination with standard antimicrobial treatment.

RELATED ART

References: Davies, Nat. Rev. Drug Discov. (2003) 2:114-122; Bjarnsholt et al., Nat. Rev. Drug Discov. (2013) 12:791-808; Wu et al. International Journal of Oral Science 7 (2015); Rasamiravaka et al. BioMed Research International Volume (2015); Bhattacharya et al. Expert Rev Anti Infect Ther. (2015) 13 (12); Peneysan et al. Molecules (2015) 20; Rabin et al. Future Med. Chem. (2015) 7 (4).

Microorganisms can occur as planktonic organisms (in particular free-floating bacteria or fungi) or as biofilm (in particular biofilm bacteria or fungi). Typically, these biofilms consist in tightly packed and highly organized communities of microorganisms encased within a secreted polymeric matrix composed of protein, extracellular DNA, amyloid fibers, and polysaccharide that form a highly hydrated polar mixture that contributes to the overall structural scaffold and architecture of the biofilm.

Compared to planktonic microorganisms, biofilm microorganisms predominate in virtually all ecosystems under sufficient-nutrient conditions. Biofilms may thus be established in various host environments, as they may adhere to abiotic surfaces, for example implant surfaces such as catheters, vascular prosthesis, prosthetic cardiac valves, cardiac pacemakers, cerebrospinal fluid shunts, urinary catheters, peritoneal dialysis catheters, joint prostheses and orthopedic fixation devices, intrauterine devices, biliary tract stents, breast implants, contact lenses, dentures, and in the dental area caries and periodontitis, as well as to biological surfaces such as lung, skin, bone, teeth, leading for example to chronic airway infections in cystic fibrosis patients, chronic obstructive pulmonary diseases, native valve endocarditis, chronic otitis media, chronic sinusitis, or chronic wound infections. Biofilm also forms dental plaque as a consequence of both bacteria and fungi adhering to the teeth and being embedded in salivary polymers and microbial extracellular products, thus favoring the development of dental diseases. Biofilms are also an issue in food industries due to the ability of biofilms to form on food equipment surfaces in food plants and during industrial processes.

If biofilm microorganisms were simply planktonic cells that had adhered to a surface, this revelation would be unimportant, but biofilm microorganisms are profoundly different to planktonic microorganisms. Biofilm polymeric matrix creates a shield against host immune defenses and protecting deep-seated bacteria and fungi from anti-bacterial and anti-fungal agents, respectively. Moreover, biofilms act as an infectious niche, favoring chronic infection and relapses. Biofilm-associated infections are chronic, persistent and difficult to cure. Even in the case of biofilm formed on implants such as cardiac valves, detached biofilm cells can migrate along with the bloodstream and cause infection in other organs.

Biofilms are involved in a wide variety of infections and formed by both Gram-positive and Gram-negative bacteria as well as mycoplasmas, spiroplasmas, and fungi. They are also involved in infections caused by ESKAPE pathogens. The number of diseases associated with biofilms is considered to be quite large, with colitis, vaginitis, urethritis, conjunctivitis and otitis being just a short list of common examples. Biofilms are, as indicated, also important as colonizers of medical devices, including urinary, venous and arterial catheters, shunts and the like. Since bacteria and fungi present in a biofilm resist antimicrobials and to immune defense mechanisms, biofilm-related infections tend to be chronic, such as bronchopulmonary *Pseudomonas aeruginosa* (*P. aeruginosa*) infections in cystic fibrosis (CF) patients.

In fact, biofilm bacteria are up to 1.000 times more resistant to antibiotics than planktonic bacteria. Traditionally, antibiotics have been developed to target cellular mechanisms involved in growth and survival of free-floating bacteria i.e. bacteria in a planktonic mode of life. Yet, biofilm bacteria greatly differ from their planktonic counterparts. Notably, the extracellular proteins, virulence factors and surfactants that biofilm bacteria express are distinct from those expressed by free-floating bacteria. Also, the protective biofilm matrix enables evasion of host immune responses, facilitating persistence, and dissemination of bacteria. Furthermore, antibacterial resistance is an inherent characteristic of biofilms. Thus, bacteria can persist despite an intact host immune defense and frequent antibiotic treatments. Furthermore, antibiotic treatments targeted to infections using only planktonic bacteria are most often ineffective against the biofilm phenotype. Effective antibiotic doses for biofilm eradication are hardly reached by conventional antibiotic administrations due to the toxicities and the side effects of high doses of antibiotics and due to the limitation of renal and hepatic functions. Moreover, exposing bacteria in a biofilm to antibiotics enhances further the selection pressure associated with the development of antibiotic resistance. Similarly, fungal biofilm-associated infections are frequently refractory to conventional therapy because of resistance to antimicrobial agents, due in part due to the surface-induced upregulation of drug efflux pumps.

Current methods may consist of physical removal of the source of infection (catheters or surgical removal of orthopedic hardware, nonadsorbable sutures, necrotic tissue) or treatment with antimicrobials. However, although antibiotic and anti-fungal agents directly target the organisms forming the biofilm, they hardly succeed in treating biofilm-associated conditions. Current methods are in fact not always successful in eradicating the infection, and infections involving biofilm-residing bacteria or fungi often turn out to be untreatable and eventually develop into a chronic state. Despite the fact that the ability to form biofilms is a universal attribute of bacteria and that many medically important fungi produce biofilms, the precise mechanisms underlying biofilm formation are still not well understood which cause biofilm-associated infections to be particularly difficult to treat and eradicate. Non-microbicidal anti-biofilm drugs in development mainly aim at (i) avoiding microbial attachment to a surface, (ii) affecting biofilm maturation and/or inducing its dispersion and degradation—for example by targeting bacterial systems and messengers that play an important role in the regulation of biofilm formation, notably bacteria quorum sensing (QS), nucleotides, in particular c-di-GMP, or small noncoding RNAs (sRNAs)—or (iii) avoiding microbial attachment to a surface, for example by damaging of amyloid structures involved in biofilm formation. Treatment of biofilm-related conditions has proven a considerable unmet clinical need.

Tailored empty liposomes such as empty liposomes composed of cholesterol (CHOL) and/or sphingomyelin (SM) and their use for the treatment of bacterial infections have recently been described to serve as traps for bacterial toxins (WO 2013/186286; Henry B D et al., Nat Biotechnol 2015; 33 (1): 81-88; Azeredo da Silveira, S and Perez, A, Expert Rev. Anti Infect. Ther. 2015; 13 (5): 531-533).

Therefore, one objective of the present invention is to provide compositions having anti-biofilm activity and compositions for the treatment of biofilm associated conditions and diseases.

SUMMARY OF THE INVENTION

We have surprisingly found that empty liposomes of defined lipid composition and the mixtures of empty liposomes of defined lipid composition in accordance with the present invention are able to prevent or reduce the formation of biofilm and to eradicate or reduce existing biofilm. In particular, it has been surprisingly found that the inventive empty liposomes and mixtures thereof proved to decrease biofilm formation by *Pseudomonas aeruginosa*. Thus, the empty liposomes and mixtures of empty liposomes of defined lipid composition in accordance with the present invention are able to prevent or reduce biofilm formation or eradicate or reduce existing biofilm and, thus, able to prevent and treat conditions and diseases such as acute and chronic bacterial infections or cystic fibrosis.

Moreover, disrupting or weakening a biofilm or avoiding or decreasing biofilm formation via the single empty liposomes or the mixtures of empty liposomes of the invention will lead to an improved efficacy of simultaneously or subsequently applied anti-microbial agents, in particular biocides (antibacterial agents), especially antibiotics, or anti-fungal agents. This is a highly synergistic effect, since liberated planktonic bacteria or fungi are much more (up to 1.000-fold) susceptible to anti-microbial agents and antibiotics. By a simultaneous or subsequent antibiotic or anti-fungal treatment, planktonic organisms can be eliminated, and spreading of the infection to other parts of the body can be avoided. Moreover, liberated organisms are much more susceptible to host's immune defense mechanisms and thus, can be cleared more effectively by the host's own immune system.

Furthermore, the believed non-toxicity of the inventive compositions and empty liposomes in accordance with the present invention represents a further beneficial and advantageous characteristic of the present invention.

Thus, in first aspect, the present invention provides for a composition for use in a method for preventing or reducing biofilm formation or for eradicating or reducing existing biofilm, wherein said composition comprises, preferably consists of, (i) a single empty liposome, wherein said single empty liposome is selected from (a) an empty liposome comprising cholesterol, wherein the amount of cholesterol is at least 30% (weight per weight), wherein preferably said empty liposome comprising, further preferably consisting of, cholesterol and sphingomyelin; or (b) an empty liposome consisting of sphingomyelin; or (ii) a mixture of empty liposomes; wherein said mixture of empty liposomes comprises, preferably consists of, at least one empty liposome selected from (a) an empty liposome comprising cholesterol, wherein the amount of cholesterol is at least 30% (weight per weight), wherein preferably said empty liposome comprising, further preferably consisting of, cholesterol and sphingomyelin; (b) an empty liposome consisting of sphingomyelin; and (c) an empty liposome comprising, preferably consisting of, phosphatidylcholine and sphingomyelin; and at least one empty liposome independently of each other selected from an empty liposome comprising, preferably consisting of, lipids or phospholipids selected from cholesterol, sphingomyelins, ceramides, phosphatidylcholines, phosphatidylethanolamines, phosphatidylserines, diacylglycerols, and phosphatidic acids containing one or two or more saturated or unsaturated fatty acids longer than 4 carbon atoms and up to 28 carbon atoms.

In a further aspect, the present invention provides for an empty liposome consisting of sphingomyelin and cholesterol, wherein the amount of cholesterol is at least 30% (weight per weight) for use in a method for preventing or reducing biofilm formation or for eradicating or reducing existing biofilm, preferably in a mammal, further preferably in a human.

In a further aspect, the present invention provides for an empty liposome consisting of sphingomyelin for use in a method for preventing or reducing biofilm formation or for eradicating or reducing existing biofilm, preferably in a mammal, further preferably in a human.

In still another aspect, the present invention provides for a mixture of empty liposomes comprising (a) first empty liposome consisting of sphingomyelin and cholesterol, wherein the amount of cholesterol is at least 30% (weight per weight); an (b) a second empty liposome consisting of sphingomyelin; for use in a method for preventing or reducing biofilm formation or for eradicating or reducing existing biofilm, preferably in a mammal, further preferably in a human.

In still another aspect, the present invention provides for a method for reducing biofilm formation or for eradicating or reducing existing biofilm comprising administering to a mammal, preferably a human, in need thereof a therapeutically effective amount of the inventive composition, the inventive single empty liposomes or the inventive mixture of empty liposomes. In still another aspect, the present invention provides for a method of preventing biofilm formation in a subject at risk comprising administering to a mammal, preferably a human, at risk, an effective amount of the inventive composition, the inventive single empty liposomes or the inventive mixture of empty liposomes. In yet another aspect, the present invention provides for a method for preventing or reducing biofilm formation or for eradicating or reducing existing biofilm comprising administering to a mammal, preferably a human, in need thereof a therapeutically effective amount of the inventive composition, the inventive single empty liposomes or the inventive mixture of empty liposomes without co-administering a standard antimicrobial treatment. Furthermore the invention relates to preventing or reducing biofilm formation or for eradicating or reducing existing biofilm comprising administering to a mammal, preferably a human, in need thereof a therapeutically effective amount of the inventive composition, the inventive single empty liposomes or the inventive mixture of empty liposomes, before, after, together or in parallel with a standard antimicrobial treatment of the infection.

Further aspects and embodiments of the present invention will become apparent as this description continues.

DESCRIPTION OF FIGURES

FIG. 1: Inhibition of *P. aeruginosa* multi-drug resistant strain 6077 biofilm by the inventive mixture of empty liposomes using a bacterial density of $1 \times 10^7$ cells/well. The graph presents the percentage of biofilm inhibition as compared to biofilm formed in the absence of empty liposomes.

DETAILED DESCRIPTION OF THE INVENTION

Unless defined otherwise, all technical and scientific terms used herein have the same meanings as commonly understood by one of ordinary skill in the art to which this invention belongs.

The term "about", as used herein shall have the meaning of +/−10%. For example about 50% shall mean 45% to 55%. Preferably, the term "about", as used herein shall have the meaning of +/−5%. For example about 50% shall mean 47.5% to 52.5%.

When the terms "a," or "an" are used herein, they mean "at least one" unless indicated otherwise. In particular, the use of the terms "a," or "an" in association with said single empty liposome, said first empty liposome and said second empty liposome to describe the empty liposomes and mixtures of empty liposomes in accordance with the present invention should typically and preferably refer to single empty liposomes and mixtures of empty liposomes comprising said first empty liposomes and said second empty liposomes.

Thus, in first aspect, the present invention provides for a composition for use in a method for preventing or reducing biofilm formation or for eradicating or reducing existing biofilm, wherein said composition comprises, preferably consists of, (i) a single empty liposome, wherein said single empty liposome is selected from (a) an empty liposome comprising cholesterol, wherein the amount of cholesterol is at least 30% (weight per weight), wherein preferably said empty liposome comprising, further preferably consisting of, cholesterol and sphingomyelin; or (b) an empty liposome consisting of sphingomyelin; or (ii) a mixture of empty liposomes; wherein said mixture of empty liposomes comprises, preferably consists of, at least one empty liposome selected from (a) an empty liposome comprising cholesterol, wherein the amount of cholesterol is at least 30% (weight per weight), wherein preferably said empty liposome comprising, further preferably consisting of, cholesterol and sphingomyelin; (b) an empty liposome consisting of sphingomyelin; and (c) an empty liposome comprising, preferably consisting of, phosphatidylcholine and sphingomyelin; and at least one empty liposome independently of each other selected from an empty liposome comprising, preferably consisting of, lipids or phospholipids selected from cholesterol, sphingomyelins, ceramides, phosphatidylcholines, phosphatidylethanolamines, phosphatidylserines, diacylglycerols, and phosphatidic acids containing one or two or more saturated or unsaturated fatty acids longer than 4 carbon atoms and up to 28 carbon atoms.

The term "empty liposome" as used herein, refers to liposomes, preferably artificial liposomes, having a mean diameter of 20 nm to 10 μm, preferably of 20 to 500 nm, and further preferably having a mean diameter of 20 nm to 400 nm, again further preferably of 40 nm to 400 nm or 20 nm to 200 nm, and consist of one or more phospholipid bilayers, and are typically and preferably unilamellar vesicles and multilamellar vesicles, more preferably small unilamellar vesicles (SUVs). In a preferred embodiment, the term "empty liposome" as used herein, typically and preferably refers to liposomes not incorporating any drug, typically and preferably to liposomes not: incorporating any pharmaceutical drug. "Incorporated/Incorporating" as used herein and when referring to the inventive empty liposomes, typically and preferably, means encapsulated/encapsulating into the cavity of the liposome, within the potential double layer of the liposome, or as part of the membrane layer of the liposome. In another preferred embodiment, the term "empty liposome" as used herein, typically and preferably refers to liposomes consisting of sphingomyelin and cholesterol or consisting of sphingomyelin in accordance with the present invention and solely further comprises water-soluble inorganic compounds and/or water-soluble organic molecules, wherein typically and preferably said water-soluble inorganic compounds and/or water-soluble organic molecules derive from the synthesis of said inventive empty liposomes, and wherein typically and preferably, said water-soluble inorganic compounds are inorganic salts preferably selected from NaCl, KCl, MgCl$_2$, and wherein said water-soluble organic molecules are buffering agents, wherein preferably said water-soluble organic molecules are selected from glucose and HEPES. Typically and preferably, said water-soluble inorganic compounds and/or water-soluble organic molecules are incorporated in the inventive empty liposomes of the present invention due to their presence during the production of the inventive empty liposomes. In another preferred embodiment, the term "empty liposome" as used herein, typically and preferably refers to liposomes consisting of sphingomyelin and cholesterol or consisting of sphingomyelin in accordance with the present invention and wherein said empty liposomes do not comprise an antioxidant. In a further preferred embodiment, the term "empty liposome" as used herein, typically and preferably refers to liposomes consisting of sphingomyelin and cholesterol or consisting of sphingomyelin in accordance with the present invention and solely further comprises water-soluble inorganic compounds and/or water-soluble organic molecules, wherein typically and preferably said water-soluble inorganic compounds and/or water-soluble organic molecules derive from the synthesis of said inventive empty liposomes, and wherein typically and preferably, said water-soluble inorganic compounds are inorganic salts preferably selected from NaCl, KCl, MgCl$_2$, and wherein said water-soluble organic molecules are buffering agents, wherein preferably said water-soluble organic molecules are selected from glucose and HEPES, and wherein said empty liposomes consisting of sphingomyelin and cholesterol or consisting of sphingomyelin in accordance with the present invention do not comprise an antioxidant.

The term "biofilm" as used herein should refer to a population of bacterial and/or fungal cells adherent to each other, to surfaces, interfaces including biotic and abiotic surfaces and interfaces, or associated to tissue or mucus. This definition also includes small and great microbial aggregates and floccules and also adherent populations within the pore spaces of porous media. The term "anti-biofilm activity" or only "anti-biofilm", as used herein, refers to prevention or reduction of biofilm formation or eradication or reduction of an existing biofilm, at least partial liberation of microorganism, preferably bacteria, or at least partially dissolving a biofilm. The term "biofilm bacteria", as used herein, refers to non-planktonic bacteria present in a biofilm.

The term "ESKAPE pathogen" as used herein should refer to a pathogen selected from *Enterococcus faecalis, Staphylococcus aureus, Klebsiella pneumoniae, Acinetobacter baumannii, P. aeruginosa* and *Enterobacter* spp.

The terms "inhibiting", "disrupting", "reducing" and "eradicating" as used herein and in reference to a biofilm or biofilm formation means complete or partial inhibition (preferably more than 20%, further preferably more than 30%, further preferably more than 50%, further preferably more than 90%, still more preferably more than 95% or even more than 99%) of biofilm formation, typically and preferably in the term of number of remaining cells, and/or development and also includes within its scope the reversal of biofilm development or processes associated with biofilm formation and/or development. With respect to the latter it preferably means disappearance of an existing biofilm at a rate that is greater than an untreated biofilm or a biofilm treated with a compound known to have no effect on biofilm stability. Further, inhibition may be permanent or temporary. In terms of temporary inhibition, biofilm formation and/or development may be inhibited for a time sufficient to produce the desired effect (for instance at least 5 days, preferably at least 10 days). Preferably, the inhibition of a biofilm is complete and/or permanent (with preferably no persisters) ("eradicating").

The term "medical device intended for insertion into a subject's body" as used herein refers to a surgically invasive device or implantable device as defined, e.g. but not limited to the European Commission DG Health and Consumer Directorate B, Unit B2 "Cosmetics and medical devices" Guidelines Relating to the Application of the Council Directive 93/42/EEC on Medical Devices.

The term "treating", "treatment" or "therapy" as used herein refers to means of obtaining a desired physiological effect. The effect may be therapeutic in terms of partially or completely curing a disease or a condition and/or symptoms attributed to the disease or the condition. The term refers to inhibiting the disease or condition, i.e. arresting its development; or ameliorating the disease or condition, i.e. causing regression of the disease or condition. The term "treating", or "treatment" as used herein and in the context of an ex-vivo method in accordance with the present invention or in the context of treating a surface with the inventive compositions such as a surface of a mammalian cell, tissue or structure, or a surface of a plant cell, tissue or structure, or a surface of a food plant, or a surface selected from a medical device or a surface intended for contact with water or an aqueous solution, should refer to and include, but not limited to, contacting, coating and applying said inventive compositions in said ex-vivo method in accordance with the present invention or to said surfaces.

The term "prophylaxis" as used herein refers to means of preventing or delaying the onset of disease or condition and/or symptoms attributed to the disease or condition.

The term "effective amount" as used herein refers to an amount of an active ingredient, typically and preferably a composition in accordance with the present invention, sufficient to effect beneficial or desired results when administered or applied to a subject or patient or a surface such as a surface of a medical device, typically and preferably intended for insertion into a subject's body, be in the context of prophylaxis or therapy. More specifically, the term "therapeutically effective amount" as used herein refers to an amount of an active ingredient, e.g., a composition in accordance with the present invention, sufficient to effect beneficial or desired results when administered to a subject or patient. A therapeutically effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with preventing or reducing biofilm formation or for eradicating or reducing existing biofilm, or the treatment of a condition or disease associated with said biofilm formation or said existing biofilm, wherein preferably said condition or disease is caused by bacteria present in said biofilm, and wherein preferably said condition or disease is selected from an infection, and wherein further preferably said infection is an airway infection, sexually-transmitted disease, meningitis, urinary infection, gastrointestinal disease, native valve endocarditis, colitis, vaginitis, urethritis, conjunctivitis, otitis, preferably otitis media, cystic fibrosis, ventilator-associated pneumonia, bacteremia, or wound infection. Of course, the therapeutically effective amount will vary depending upon the particular subject and condition being treated, the weight and age of the subject, the severity of the disease condition, the particular composition chosen, the dosing regimen to be followed, timing of administration, the manner of administration and the like, all of which can readily be determined by one of ordinary skill in the art.

As used herein, the terms "subject" or "animal" or "patient" or "mammal," refers to any subject, particularly a mammalian subject, for whom diagnosis, prognosis, prophylaxis or therapy is desired, for example, a human or a domesticated mammal such as a dog, cat or horse or a food animal such as a cow or sheep or pig, preferably to a human.

In a preferred embodiment, said at least one empty liposome independently of each other selected from an empty liposome comprising, preferably consisting of, lipids or phospholipids selected from cholesterol, sphingomyelins, ceramides, phosphatidylcholines, phosphatidylethanolamines, phosphatidylserines, diacylglycerols, and phosphatidic acids containing one or two or more saturated or unsaturated fatty acids longer than 4 carbon atoms and up to 28 carbon atoms is selected from (a) an empty liposome comprising cholesterol, wherein the amount of cholesterol is at least 30% (weight per weight), wherein preferably said empty liposome comprising, further preferably consisting of, cholesterol and sphingomyelin; (b) an empty liposome consisting of sphingomyelin; and (c) an empty liposome comprising, preferably consisting of, phosphatidylcholine and sphingomyelin.

In a preferred embodiment, said (i) single empty liposome is selected from (a) an empty liposome comprising cholesterol and sphingomyelin, wherein the amount of cholesterol is at least 30% (weight per weight); or (b) an empty liposome consisting of sphingomyelin; and wherein said mixture of empty liposomes comprises (a) a first empty liposome comprising cholesterol and sphingomyelin, wherein the amount of cholesterol is at least 30% (weight per weight); and (b) a second empty liposome consisting of sphingomyelin.

In a preferred embodiment, said (i) single empty liposome is selected from (a) an empty liposome consisting of sphingomyelin and cholesterol, wherein the amount of cholesterol is at least 30% (weight per weight); or (b) an empty liposome consisting of sphingomyelin; and wherein said mixture of empty liposomes comprises (a) a first empty liposome consisting of sphingomyelin and cholesterol, wherein the amount of cholesterol is at least 30% (weight per weight); and (b) a second empty liposome consisting of sphingomyelin.

In a preferred embodiment, said composition comprises, preferably consists of, a single empty liposome is selected from (a) an empty liposome comprising cholesterol and sphingomyelin, wherein the amount of cholesterol is at least 30% (weight per weight).

In a preferred embodiment, said composition for use in a method in accordance with the invention comprises, preferably consists of, a single empty liposome, wherein said single empty liposome is selected from (a) an empty liposome consisting of sphingomyelin and cholesterol, wherein the amount of cholesterol is at least 30% (weight per weight); or (b) an empty liposome consisting of sphingomyelin.

In another preferred embodiment, said composition for use in a method in accordance with the invention comprises, preferably consists of, a single empty liposome, wherein said single empty liposome is an empty liposome consisting of sphingomyelin and cholesterol, wherein the amount of cholesterol is at least 30% (weight per weight). Preferably, the amount of cholesterol of said empty liposome is 30%-70% (weight per weight), further preferably the amount of cholesterol of said empty liposome is 35%-60% (weight per weight). In another preferred embodiment, the amount of cholesterol of said empty liposome is 45%-55% (weight per weight), and again further preferably said amount of cholesterol of said empty liposome is about 50% (weight per weight). Thus, in a very preferred embodiment of the present invention, said single empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human.

In another preferred embodiment, said composition for use in said method in accordance with the invention comprises, preferably consists of, a single empty liposome, wherein said single empty liposome is an empty liposome consisting of sphingomyelin.

In an embodiment, said composition comprises, preferably consists of, a mixture of empty liposomes, wherein said mixture of empty liposomes comprises, preferably consists of, (a) a first empty liposome comprising cholesterol, wherein the amount of cholesterol is at least 30% (weight per weight); and (b) a second empty liposome consisting of sphingomyelin; and (c) a third empty liposome comprising, preferably consisting of, phosphatidylcholine and sphingomyelin.

In another embodiment, said composition for use comprises, preferably consists of, a mixture of empty liposomes, wherein said mixture of empty liposomes comprises, preferably consists of, (a) a first empty liposome comprising cholesterol, wherein the amount of cholesterol is at least 30% (weight per weight); and (b) a second empty liposome consisting of sphingomyelin; and optionally (c) an empty liposome comprising, preferably consisting of, phosphatidylcholine and sphingomyelin; and further optionally (d) at least one empty liposome independently of each other selected from an empty liposome comprising, preferably consisting of, lipids or phospholipids selected from cholesterol, sphingomyelins, ceramides, phosphatidylcholines, phosphatidylethanol-amines, phosphatidylserines, diacylglycerols, and phosphatidic acids containing one or two or more saturated or unsaturated fatty acids longer than 4 carbon atoms and up to 28 carbon atoms.

In an embodiment, said composition comprises, preferably consists of, a mixture of empty liposomes, wherein said mixture of empty liposomes comprises, preferably consists of, (a) a first empty liposome consisting of sphingomyelin and cholesterol, wherein the amount of cholesterol is at least 30% (weight per weight); and (b) a second empty liposome consisting of sphingomyelin; and (c) a third empty liposome comprising, preferably consisting of, phosphatidylcholine and sphingomyelin.

In an embodiment, said composition comprises, preferably consists of, a mixture of empty liposomes, wherein said mixture of empty liposomes comprises, preferably consists of, (a) a first empty liposome consisting of sphingomyelin and cholesterol, wherein the amount of cholesterol is at least 30% (weight per weight); and (b) a second empty liposome consisting of sphingomyelin; and (c) a third empty liposome comprising, preferably consisting of, lipids or phospholipids selected from cholesterol, sphingomyelins, ceramides, phosphatidylcholines, phosphatidylethanolamines, phosphatidylserines, diacylglycerols, and phosphatidic acids containing one or two or more saturated or unsaturated fatty acids longer than 4 carbon atoms and up to 28 carbon atoms.

In a preferred embodiment, said composition comprises, preferably consists of, a mixture of empty liposomes, wherein said mixture of empty liposomes comprises, preferably consists of, (a) a first empty liposome comprising cholesterol and sphingomyelin, wherein the amount of cholesterol is at least 30% (weight per weight); and (b) a second empty liposome consisting of sphingomyelin.

In another preferred embodiment, said composition for use in a method in accordance with the invention comprises, preferably consists of a mixture of empty liposomes, wherein said mixture of empty liposomes comprises (a) a first empty liposome consisting of sphingomyelin and cholesterol, wherein the amount of cholesterol is at least 30% (weight per weight); and (b) a second empty liposome consisting of sphingomyelin. Preferably, the amount of cholesterol of said first empty liposome is 30%-70% (weight per weight), further preferably the amount of cholesterol of said first empty liposome is 35%-60% (weight per weight). In another preferred embodiment, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human.

In another preferred embodiment, said composition for use in a method in accordance with the invention comprises a mixture of empty liposomes, wherein said mixture of empty liposomes consists of (a) a first empty liposome consisting of sphingomyelin and cholesterol, wherein the amount of cholesterol is at least 30% (weight per weight), preferably 30%-70% (weight per weight); and (b) a second empty liposome consisting of sphingomyelin. Preferably, the amount of cholesterol of said first empty liposome is 35%-60% (weight per weight), further preferably, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome of said mixture of empty liposomes consists of 50% (weight per weight) sphingomyelin and of 50% (weight per weight) cholesterol for use in a method for preventing or reducing biofilm formation or for eradicating or reducing existing biofilm, preferably in a mammal, further preferably in a human.

In another preferred embodiment, said composition for use in a method in accordance with the invention consists of a mixture of empty liposomes, wherein said mixture of empty liposomes consists of (a) a first empty liposome consisting of sphingomyelin and cholesterol, wherein the amount of cholesterol is at least 30% (weight per weight), preferably 30%-70% (weight per weight); and (b) a second empty liposome consisting of sphingomyelin.

Preferably, the amount of cholesterol of said first empty liposome is 35%-60% (weight per weight), further preferably, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome of said mixture of empty liposomes consists of 50% (weight per weight) sphingomyelin and of 50% (weight per weight) cholesterol for use in a method for preventing or reducing biofilm formation or for eradicating or reducing existing biofilm, preferably in a mammal, further preferably in a human.

In another preferred embodiment, said mixture of empty liposomes comprises at least 1%, preferably at least 5%, further preferably at least 10%, again further preferably at least 20%, again further preferably at least 30% (weight per weight) of said first empty liposome and at most 99%, preferably at most 95%, further preferably at most 90%, again further preferably at most 80%, again further preferably at most 70% (weight per weight) of said second empty liposome, and wherein again further preferably said mixture of empty liposomes comprises at least 40% (weight per weight) of said first empty liposome and at most 60% (weight per weight) of said second empty liposome.

In another preferred embodiment, said mixture of empty liposomes comprises at least 1%, preferably at least 5%, further preferably at least 10%, again further preferably at least 20%, again further preferably at least 30% (weight per weight) of said second empty liposome and at most 99%, preferably at most 95%, further preferably at most 90%, again further preferably at most 80%, again further preferably at most 70% (weight per weight) of said first empty liposome, and wherein again further preferably said mixture of empty liposomes comprises at least 40% (weight per weight) of said second empty liposome and at most 60% (weight per weight) of said first empty liposome.

In another preferred embodiment, said mixture of empty liposomes comprises 1-99%, preferably 5%-95%, further preferably 10-90%, again further preferably 20-80%, again further preferably 30-70% (weight per weight) of said first and of said second empty liposome, and wherein again further preferably said mixture of empty liposomes comprises 40%-60% (weight per weight) of said first and said second empty liposome.

In another preferred embodiment, said mixture of empty liposomes comprises at least 30% (weight per weight) of said first empty liposome and at most 70% (weight per weight) of said second empty liposome, and wherein preferably said mixture of empty liposomes comprises at least 40% (weight per weight) of said first empty liposome and at most 60% (weight per weight) of said second empty liposome. In a further preferred embodiment, said mixture of empty liposomes comprises at least 45% (weight per weight) of said first empty liposome and at most 55% (weight per weight) of said second empty liposome, and wherein preferably said mixture of empty liposomes comprises about 50% (weight per weight) of said first empty liposome and about 50% (weight per weight) of said second empty liposome.

In another preferred embodiment, said mixture of empty liposomes comprises at least 30% (weight per weight) of said second empty liposome and at most 70% (weight per weight) of said first empty liposome, and wherein preferably said mixture of empty liposomes comprises at least 40% (weight per weight) of said second empty liposome and at most 60% (weight per weight) of said first empty liposome. In a further preferred embodiment, said mixture of empty liposomes comprises at least 45% (weight per weight) of said second empty liposome and at most 55% (weight per weight) of said first empty liposome. and wherein preferably said mixture of empty liposomes comprises about 50% (weight per weight) of said second empty liposome and about 50% (weight per weight) of said first empty liposome.

In another preferred embodiment, said mixture of empty liposomes comprises at least 20% (weight per weight) of said first and said second empty liposome, and wherein preferably said mixture of empty liposomes comprises at least 30% (weight per weight) of said first and said second empty liposome. In a further preferred embodiment said mixture of empty liposomes comprises at least 40% (weight per weight) of said first and said second empty liposome.

In another preferred embodiment, said mixture of empty liposomes comprises at least 20% (weight per weight) of each of said first and said second empty liposome, and wherein preferably said mixture of empty liposomes comprises at least 30% (weight per weight) of each of said first and said second empty liposome. In a further preferred embodiment said mixture of empty liposomes comprises at least 40% (weight per weight) of each of said first and said second empty liposome.

In another preferred embodiment, said mixture of empty liposomes consists of said first empty liposome and said second empty liposome.

In a further preferred embodiment, said mixture of empty liposomes consists of said first empty liposome and said second empty liposome, and wherein said mixture of empty liposomes consists of at least 40% (weight per weight) of said first empty liposome and at most 60% (weight per weight) of said second empty liposome, and wherein preferably said mixture of empty liposomes consists of about 50% (weight per weight) of said first empty liposome and about 50% (weight per weight) of said second empty liposome.

In a further preferred embodiment, said mixture of empty liposomes consists of said first empty liposome and said second empty liposome, and wherein said mixture of empty liposomes consists of at least 40% (weight per weight) of said second empty liposome and at most 60% (weight per weight) of said first empty liposome, and wherein preferably said mixture of empty liposomes consists of about 50% (weight per weight) of said second empty liposome and about 50% (weight per weight) of said first empty liposome.

In another preferred embodiment, said mixture of empty liposomes consists of 1-99%, preferably 5%-95%, further preferably 10-90%, again further preferably 20-80%, again further preferably 30-70% (weight per weight) of said first and of said second empty liposome, and wherein again further preferably said mixture of empty liposomes consists of 40%-60% (weight per weight) of said first and said second empty liposome.

In a further preferred embodiment, said mixture of empty liposomes consists of said first empty liposome and said second empty liposome, and wherein said mixture of empty liposomes consists of at least 40% (weight per weight) of said first empty liposome and at most 60% (weight per weight) of said second empty liposome, and wherein preferably said mixture of empty liposomes consists of about 50% (weight per weight) of said first empty liposome and about 50% (weight per weight) of said second empty liposome, and wherein the amount of cholesterol of said first empty liposome is 45%-55% (weight per weight), and wherein preferably said the amount of cholesterol of said first empty liposome is about 50% (weight per weight).

In a further preferred embodiment, said mixture of empty liposomes consists of said first empty liposome and said second empty liposome, and wherein said mixture of empty liposomes consists of at least 40% (weight per weight) of said second empty liposome and at most 60% (weight per weight) of said first empty liposome, and wherein preferably said mixture of empty liposomes consists of about 50% (weight per weight) of said second empty liposome and about 50% (weight per weight) of said first empty liposome, and wherein the amount of cholesterol of said first empty liposome is 45%-55% (weight per weight), and wherein preferably said the amount of cholesterol of said first empty liposome is about 50% (weight per weight).

In a further preferred embodiment, the empty liposomes used or for use in the present invention, are liposomes, preferably artificial liposomes, having a mean diameter of 20 nm to 10 μm, preferably of 20 to 500 nm, and further preferably having a mean diameter of 20 nm to 200 nm. Empty liposomes used or for use in the present invention are liposomes not encapsulating any drug. Empty liposomes used or for use in the present invention do not comprise any drug. Empty liposomes used or for use in the present invention do not incorporate other drugs. "Incorporated" as used herein, typically and preferably means encapsulated into the cavity of the liposome, within the potential double layer of the liposome, or as part of the membrane layer of the liposome. The liposomes used or for use in the present invention consist of one or more phospholipid bilayers, typically and preferably unilamellar and multilamellar vesicles. Most preferred are small unilamellar vesicles (SUVs).

In a further aspect, the present invention provides for an empty liposome consisting of sphingomyelin and cholesterol, wherein the amount of cholesterol is at least 30% (weight per weight) for use in a method for preventing or reducing biofilm formation or for eradicating or reducing existing biofilm, preferably in a mammal, and further preferably in a human. In another preferred embodiment, said empty liposome for use in a method in accordance with the invention comprises, preferably consists of, sphingomyelin and cholesterol, wherein the amount of cholesterol is 30%-70% (weight per weight), further preferably the amount of cholesterol of said empty liposome is 35%-60% (weight per weight). In another preferred embodiment, the amount of cholesterol of said empty liposome is 45%-55% (weight per weight), and again further preferably the amount of cholesterol of said empty liposome is about 50% (weight per weight). Thus, in a very preferred embodiment of the present invention, said empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human.

In a further aspect, the present invention provides for an empty liposome consisting of sphingomyelin for use in a method for preventing or reducing biofilm formation or for eradicating or reducing existing biofilm, preferably in a mammal, further preferably in a human.

In still another aspect, the present invention provides for a mixture of empty liposomes comprising (a) first empty liposome consisting of sphingomyelin and cholesterol, wherein the amount of cholesterol is at least 30% (weight per weight); an (b) a second empty liposome consisting of sphingomyelin; for use in a method for preventing or reducing biofilm formation or for eradicating or reducing existing biofilm, preferably in a mammal, further preferably in a human. Preferably, the amount of cholesterol of said first empty liposome is 30%-70% (weight per weight), further preferably the amount of cholesterol of said first empty liposome is 35%-60% (weight per weight). In another preferred embodiment, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human. In another preferred embodiment, said mixture of empty liposomes comprises at least 30% (weight per weight) of said first empty liposome and at most 70% (weight per weight) of said second empty liposome, and wherein preferably said mixture of empty liposomes comprises at least 40% (weight per weight) of said first empty liposome and at most 60% (weight per weight) of said second empty liposome. In a further preferred embodiment, said mixture of empty liposomes comprises at least 45% (weight per weight) of said first empty liposome and at most 55% (weight per weight) of said second empty liposome, and wherein preferably said mixture of empty liposomes comprises about 50% (weight per weight) of said first empty liposome and about 50% (weight per weight) of said second empty liposome.

In still another aspect, the present invention provides for a mixture of empty liposomes comprising (a) first empty liposome consisting of sphingomyelin and cholesterol, wherein the amount of cholesterol is at least 30% (weight per weight); an (b) a second empty liposome consisting of sphingomyelin; for use in a method for preventing or reducing biofilm formation or for eradicating or reducing existing biofilm, preferably in a mammal, further preferably in a human. Preferably, the amount of cholesterol of said first empty liposome is 30%-70% (weight per weight), further preferably the amount of cholesterol of said first empty liposome is 35%-60% (weight per weight). In another preferred embodiment, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human. In another preferred embodiment, said mixture of empty liposomes comprises at least 30% (weight per weight) of said second empty liposome and at most 70% (weight per weight) of said first empty liposome, and wherein preferably said mixture of empty liposomes comprises at least 40% (weight per weight) of said second empty liposome and at most 60% (weight per weight) of said first empty liposome. In a further preferred embodiment, said mixture of empty liposomes comprises at least 45% (weight per weight) of said second empty liposome and at most 55% (weight per weight) of said first empty liposome, and wherein preferably said mixture of empty liposomes comprises about 50% (weight per weight) of said second empty liposome and about 50% (weight per weight) of said first empty liposome.

In still another aspect, the present invention provides for a mixture of empty liposomes comprising (a) first empty liposome consisting of sphingomyelin and cholesterol, wherein the amount of cholesterol is at least 30% (weight per weight); an (b) a second empty liposome consisting of sphingomyelin; for use in a method for preventing or reducing biofilm formation or for eradicating or reducing existing biofilm, preferably in a mammal, further preferably in a human. Preferably, the amount of cholesterol of said first empty liposome is 30%-70% (weight per weight), further preferably the amount of cholesterol of said first empty liposome is 35%-60% (weight per weight). In another preferred embodiment, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human. In another preferred embodiment, said mixture of empty liposomes comprises 1-99%, preferably 5%-95%, further preferably 10-90%, again further preferably 20-80%, again further preferably 30-70% (weight per weight) of said first and of said second empty liposome, and wherein again further preferably said mixture of empty liposomes comprises 40%-60% (weight per weight) of said first and said second empty liposome.

Thus, in another aspect, the present invention provides for a composition comprising, preferably consisting of, a mixture of empty liposomes, wherein said mixture of empty liposomes comprises, preferably consists of, (a) first empty liposome consisting of sphingomyelin and cholesterol, wherein the amount of cholesterol is at least 30% (weight per weight); an (b) a second empty liposome consisting of sphingomyelin; for use in a method for preventing or reducing biofilm formation or for eradicating or reducing existing biofilm, preferably in a mammal, further preferably in a human. Preferably, the amount of cholesterol of said first empty liposome is 30%-70% (weight per weight), further preferably the amount of cholesterol of said first empty liposome is 35%-60% (weight per weight). In another preferred embodiment, the amount of cholesterol of said first empty liposome is 45%-55% (weight per weight), and again further preferably said amount of cholesterol of said first empty liposome is about 50% (weight per weight). Thus, in a very preferred embodiment of the present invention, said first empty liposome comprises, preferably consists of 50% (weight per weight) sphingomyelin and of 50% (weight per weight) cholesterol for use in a method for preventing or reducing biofilm formation or for eradicating or reducing existing biofilm, preferably in a mammal, further preferably in a human. In another preferred embodiment, said mixture of empty liposomes comprises 1-99%, preferably 5%-95%, further preferably 10-90%, again further preferably 20-80%, again further preferably 30-70% (weight per weight) of said first and of said second empty liposome, and wherein again further preferably said mixture of empty liposomes comprises 40%-60% (weight per weight) of said first and said second empty liposome.

Thus, in a very preferred embodiment of the present invention, said mixture of empty liposomes comprises, preferably consists of, (i) a first empty liposome consisting of about 50% (weight per weight) sphingomyelin and of about 50% (weight per weight) cholesterol, and (ii) a second empty liposome consisting of (100%) sphingomyelin; wherein said mixture of empty liposomes comprises at least 45% (weight per weight) of said first empty liposome and at most 55% (weight per weight) of said second empty liposome, and wherein preferably said mixture of empty liposomes comprises about 50% (weight per weight) of said first empty liposome and about 50% (weight per weight) of said second empty liposome for use in a method for preventing or reducing biofilm formation or for eradicating or reducing existing biofilm, preferably in a mammal, further preferably in a human.

Thus, in another aspect, the present invention provides for a composition comprising, preferably consisting of, a mixture of empty liposomes, wherein said mixture of empty liposomes comprises, preferably consists of, (i) a first empty liposome consisting of about 50% (weight per weight) sphingomyelin and of about 50% (weight per weight) cholesterol, and (ii) a second empty liposome consisting of (100%) sphingomyelin; wherein said mixture of empty liposomes comprises at least 45% (weight per weight) of said first empty liposome and at most 55% (weight per weight) of said second empty liposome, and wherein preferably said mixture of empty liposomes comprises about 50% (weight per weight) of said first empty liposome and about 50% (weight per weight) of said second empty liposome for use in a method for preventing or reducing biofilm formation or for eradicating or reducing existing biofilm, preferably in a mammal, further preferably in a human.

In a further preferred embodiment, said first empty liposome consisting of about 50% (weight per weight) sphingomyelin and of about 50% (weight per weight) cholesterol, and said second empty liposome consisting of (100%) sphingomyelin, comprises a mean diameter of 20 to 500 nm, preferably of 20 nm to 400 nm, again further preferably of 40 nm to 400 nm. In a further preferred embodiment, said first empty liposome consisting of about 50% (weight per weight) sphingomyelin and of about 50% (weight per weight) cholesterol, and said second empty liposome consisting of (100%) sphingomyelin, comprises a pH of 6.6-8.0. In a further preferred embodiment, said first empty liposome consisting of about 50% (weight per weight) sphingomyelin and of about 50% (weight per weight) cholesterol, and said second empty liposome consisting of (100%) sphingomyelin, comprises a poly dispersity index of <0.45. In a further preferred embodiment, said first empty liposome consisting of about 50% (weight per weight) sphingomyelin and of about 50% (weight per weight) cholesterol, and said second empty liposome consisting of (100%) sphingomyelin, comprises a zeta potential of −25 to +2 mV.

The liposomes are manufactured according to extrusion or sonication or microfluidization (e.g. high pressure homogenization) methods known in the art. For example, the lipids are mixed in an organic solvent such as chloroform. Chloroform is evaporated and the dry lipid film is hydrated in an aqueous solution such as normal saline (0.9% NaCl), Krebs solution, or Tyrode's solution and further sonicated to produce liposomes. If necessary, the size of the liposomes can be controlled by their extrusion through membrane filters of fixed pore diameter. Individually produced liposomes of different lipid compositions are mixed in the required proportions typically and preferably just before application. As another example, liposomes are prepared using standard liposome hydration, extrusion, and diafiltration processes, in which lipids are dissolved in solvent such as ethanol while mixing, then the lipid solution is added to PBS Buffer Solution while mixing for liposomes of heterogeneous size to spontaneously form and fully hydrate. The resulting vesicles are extruded repeatedly through a series of polycarbonate track-etched membranes until the desired particle size is achieved, as measured by dynamic light scattering. The Post Extrusion process fluid is diafiltered against PBS to remove solvent from the process fluid and finally concentrated and/or diluted to a target concentration of total lipid with PBS Buffer Solution.

The lipid surface (bilayer) of liposomes forms spontaneously in water-based solvents and therefore traps water and other water-soluble inorganic and organic molecules, which might be present during liposome production, inside the liposome. The empty liposomes, used in the present study, are liposomes produced in buffers containing water and simple organic or inorganic molecules (for example NaCl, KCl, $MgCl_2$, glucose, HEPES, and/or $CaCl_2$)).

In a very preferred embodiment of the present invention, the composition comprises, preferably consist of, a mixture of empty liposomes comprising (a) first empty liposome consisting of sphingomyelin and cholesterol, wherein the amount of cholesterol is about 50% (weight per weight); an (b) a second empty liposome consisting of sphingomyelin; for use in a method for preventing or reducing biofilm formation or for eradicating or reducing existing biofilm, preferably in a mammal, further preferably in a human, again further preferably for use in a method for preventing or reducing biofilm formation in a human. Preferably, said mixture of empty liposomes comprises at least 40% (weight per weight) of said first empty liposome and at most 60% (weight per weight) of said second empty liposome. More preferably, said mixture of empty liposomes comprises about 50% (weight per weight) of said first empty liposome and about 50% (weight per weight) of said second empty liposome.

In another preferred embodiment, said use is in a method for preventing or reducing biofilm formation, wherein preferably said use is in a method for preventing or reducing biofilm formation on a surface; preferably, said surface is a surface of a mammalian, preferably human, cell, tissue or structure, and wherein further preferably said cell or tissue is lung, muscle, bone or skin cell or tissue, and said structure is a tooth.

In another preferred embodiment, said use is in a method for preventing or reducing biofilm formation in a mammal, preferably in a human, wherein further preferably said use is in a method for preventing or reducing biofilm formation on a surface in a mammal, preferably in a human.

In another preferred embodiment, said use is in a method for eradicating or reducing an existing biofilm, wherein preferably said use is in a method for preventing or reducing biofilm formation on a surface; preferably, said surface is a surface of a mammalian, preferably human, cell, tissue or structure, and wherein further preferably said cell or tissue is lung, muscle, bone or skin cell or tissue, and said structure is a tooth.

In another preferred embodiment, said use is in a method for preventing or reducing biofilm formation on a surface or for use in a method for eradicating or reducing an existing biofilm on a surface.

In another preferred embodiment, said use is in a method for preventing or reducing biofilm formation on a surface, preferably, said surface is a surface of a mammalian cell, tissue or structure.

In another preferred embodiment, said use is in a method for preventing or reducing biofilm formation on a surface, preferably, said surface is a surface of a plant cell, tissue or structure. In another preferred embodiment the plant may be, but is not limited to, a plant producing carrots, potatoes, cucumbers, onions, tomatoes, lettuce, apples, citrus fruit or plums. In certain embodiments, the plant cell is derived from and the tissue or structure is selected from a leaf, a root, a flower, a fruit, or other edible structures of a plant. In another preferred embodiment, said surface is a surface of a food plant.

In another preferred embodiment, said use is in a method for eradicating or reducing an existing biofilm on a surface; preferably, said surface is a surface of a mammalian, preferably human, cell, tissue or structure, and wherein further preferably said cell or tissue is lung, muscle, bone or skin cell or tissue, and said structure is a tooth.

In another preferred embodiment, said surface is a surface of a wound dressing.

In another preferred embodiment, said surface is a, typically and preferably abiotic, surface selected from a medical device or a surface intended for contact with water or an aqueous solution.

In another preferred embodiment, said surface is a, typically and preferably abiotic, surface of a medical device, typically and preferably intended for insertion into a subject's body, wherein said medical device is selected from a pacemaker, pacemaker lead, catheter, stent, vascular prosthesis, prosthetic cardiac valve, cardiac pacemaker, cerebrospinal fluid shunt, urinary catheter, peritoneal dialysis catheters, joint prosthesis and orthopaedic fixation device, intrauterine device, biliary tract stent, breast implant, contact lens, denture.

In another preferred embodiment, said surface is a surface intended for contact with water or an aqueous solution, wherein said surface intended for contact with water or an aqueous solution is a the surface of a ship hull, a pipe, a filter, a strain or a pump, and wherein preferably said surface is of stainless steel or polypropylene.

In certain preferred embodiments, the medical device intended for insertion into a subject's body is a surgically invasive device intended for short-term use (>60 minutes, <30 days), such as, but not limited to, clamps, infusion cannulae, skin closure devices, temporary filling materials, tissue stabilisers used in cardiac surgery, cardiovascular catheters, cardiac output probes, temporary pacemaker leads, thoracic catheters intended to drain the heart, including the pericardium, carotid artery shunts, ablation catheter, neurological catheters, cortical electrodes or brachytherapy devices.

In certain preferred embodiments, the medical device intended for insertion into a subject's body is an implantable device or long-term surgically invasive device (>30 days), such as prosthetic joint replacements, ligaments, shunts, stents and valves (e.g. pulmonary valves), nails and plates, intraocular lenses, internal closure devices (including vascular closure devices), tissue augmentation implants, peripheral vascular catheters, peripheral vascular grafts and stents, penile implants, non-absorbable sutures, bone cements and maxilla-facial implants, visco-elastic surgical devices intended specifically for ophthalmic anterior segment surgery, bridges and crowns, dental filling materials and pins, dental alloys, ceramics and polymers, prosthetic heart valves, aneurysm clips, vascular prosthesis and stents, central vascular catheters, spinal stents, CNS electrodes, cardiovascular sutures, permanent and retrievable vena cava filters, septal occlusion devices, intra-aortic balloon pumps, external left ventricular assisting devices.

In the case of the food processing industry, biofilm causes chronic bacterial contamination in food processing equipment such as pasteurization pipes and tubes.

In the case of marine-based industries, marine fouling is typically described as comprising several stages, with the early step of bacterial adhesion initiating the formation of a biofilm, which is then followed by secondary colonizers of spores of macroalgae (e.g. enteromorpha intestinalis, ulothrix) and protozoans (e.g. *vorticella, Zoothamnium* sp.) that attach themselves. Lastly, tertiary colonizers—the macrofoulers attach including tunicates, mollusks and sessile Cnidarians. Thus, biofilm formation provides a substratum for biofouling of submerged surfaces such as ship hulls, boat propellers, cages, underwater dock structures, underwater structures on offshore oil platforms, submarine mines, buoys, submarine cables, cooling systems of power plants, pipes and filters of desalination plants etc.

In another preferred embodiment, said use is in a method for preventing or reducing bacteria biofilm formation on a surface.

The biofilm dwelling bacteria may be any bacteria, i.e. Gram-negative or Gram-positive bacteria or mycoplasmas and spiroplasmas. Within these groups there are bacteria that associate with animal cells, plant cells or artificial surfaces. In certain embodiments, the bacteria producing and/or residing in the biofilms discussed herein are Gram-negative bacteria or Gram-positive bacteria.

In another preferred embodiment, said use is for prophylaxis or treatment of a condition or disease, and wherein preferably said condition or disease is caused by bacteria present in said biofilm.

In another preferred embodiment, said use is for prophylaxis, typically and preferably of a condition or disease, and wherein further preferably said condition or disease is caused by bacteria present in said biofilm. In another preferred embodiment, said use is for therapy of a condition or disease, and wherein preferably said condition or disease is caused by bacteria present in said biofilm.

In another preferred embodiment, said use is for prophylaxis or therapy of a condition or disease, and wherein said condition or disease is an infectious disease. In another preferred embodiment, said use is for prophylaxis, typically and preferably, of a condition or disease, and wherein said condition or disease is an infectious disease. In another preferred embodiment, said use is for therapy of a condition or disease, and wherein said condition or disease is an infectious disease.

In another preferred embodiment, said use is for prophylaxis or therapy of a condition or disease of a mammal, preferably of a human, and wherein preferably said condition or disease is an infectious disease. In another preferred embodiment, said use is for therapy of a condition or disease of a mammal, preferably of a human, and wherein preferably said condition or disease is an infectious disease.

In another preferred embodiment, said condition or disease is selected from an infection, and wherein preferably said infection is an airway infection, sexually-transmitted disease, meningitis, urinary infection, gastrointestinal disease, native valve endocarditis, colitis, vaginitis, urethritis, conjunctivitis, otitis, preferably otitis media, cystic fibrosis, ventilator-associated pneumonia, bacteremia, or wound infection.

In another preferred embodiment, said condition or disease is an airway infection, sexually-transmitted disease, meningitis, urinary infection, gastrointestinal disease, native valve endocarditis, colitis, vaginitis, urethritis, conjunctivitis, otitis, preferably otitis media, cystic fibrosis, ventilator-associated pneumonia, bacteremia, or wound infection.

In another preferred embodiment, said condition or disease is an infection.

In another preferred embodiment, said condition or disease is selected from an airway infection, sexually-transmitted disease, meningitis, urinary infection, gastrointestinal disease, native valve endocarditis, colitis, vaginitis, urethritis, conjunctivitis, otitis, preferably otitis media, cystic fibrosis, ventilator-associated pneumonia, bacteremia, or wound infection.

In another preferred embodiment, said condition or disease is an airway infection. In another preferred embodiment, said condition or disease is a sexually-transmitted disease. In another preferred embodiment, said condition or disease is meningitis. In another preferred embodiment, said condition or disease is an urinary infection. In another preferred embodiment, said condition or disease is a gastrointestinal disease. In another preferred embodiment, said condition or disease is native valve endocarditis. In another preferred embodiment, said condition or disease is colitis. In another preferred embodiment, said condition or disease is vaginitis. In another preferred embodiment, said condition or disease is urethritis. In another preferred embodiment, said condition or disease is conjunctivitis. In another preferred embodiment, said condition or disease is otitis, preferably otitis media. In another preferred embodiment, said condition or disease is ventilator-associated pneumonia. In another preferred embodiment, said condition or disease is bacteremia. In another preferred embodiment, said condition or disease is a (chronic) wound infection, typically and preferably a chronic wound infection.

In another preferred embodiment, said condition or disease is a chronic airway infection, preferably said chronic airway infection is cystic fibrosis, a chronic obstructive pulmonary disease or chronic sinusitis. In another preferred embodiment, said condition or disease is cystic fibrosis.

In another preferred embodiment, said condition or disease is caused by bacteria, mycoplasmas, spiroplasmas, or fungi. In another preferred embodiment, said condition or disease is caused by bacteria. In another preferred embodiment, said condition or disease is caused by mycoplasmas. In another preferred embodiment, said condition or disease is caused by spiroplasmas. In another preferred embodiment, said condition or disease is caused by fungi, wherein preferably said fungi are selected from *Candida, Aspergillus, Cryptococcus, Trichosporon, Coccidioides* or *Pneumocystis*.

Infections and conditions involving biofilm include infections caused by Gram-positive bacteria such as *S. pneumoniae, Bacillus* spp, *Listeria monocytogenes, Staphylococcus* spp, lactic acid bacteria, including *Lactobacillus plantarum* and *Lactococcus lactis, Streptococcus sobrinus, Streptococcus mutans*, by Gram-negative bacteria such as *Escherichia coli, Pseudomonas aeruginosa*, Entersobacteriaceae, *Salmonella* species, *Actinobacillus pleuropneumoniae, Proteus mirabilis, Acinetobacter baumannii, Shigella species, Moraxella, Helicobacter, Stenotrophomonas*, Bdellovibrio, acetic acid bacteria, *Legionella*, cyanobacteria, spirochaetes, green sulfur, and green non-sulfur bacteria, *Neisseria, Haemophilus* influenza, *Klebsiella pneumoniae, Serratia marcescens*), as well as by mycoplasmas, spiroplasmas, and fungi such as *Candida, Aspergillus, Cryptococcus, Trichosporon, Coccidioides, Pneumocystis*. Some pathogens forming biofilm are ESKAPE pathogens. Infections and conditions involving biofilm include for example those caused by Gram-negative cocci responsible for sexually transmitted diseases (e.g. *Neisseria gonorrhoeae*), for meningitis (e.g.

*Neisseria meningitidis*), or for respiratory symptoms (e.g. *Moraxella catarrhalis, Haemophilus influenzae*). They also include infections and conditions caused by Gram-negative bacilli responsible for primarily respiratory problems (e.g. *Klebsiella pneumoniae, Legionella pneumophila, Pseudomonas aeruginosa*), for primarily urinary problems (e.g. *Escherichia coli, Proteus mirabilis, Enterobacter cloacae, Serratia marcescens*), or for primarily gastrointestinal problems (e.g. *Helicobacter pylori, Salmonella enteritidis, Salmonella typhi*). Infections involving biofilm include also hospital-acquired infections (e.g. *Acinetobacter baumannii*) responsible for bacteraemia, secondary meningitis, and ventilator-associated pneumonia in hospitals and intensive-care units.

In another preferred embodiment, said condition or disease, preferably said infection, is caused by at least one ESKAPE pathogen.

In another preferred embodiment, said condition or disease, preferably said infection, is caused by *Enterococcus faecalis*. In another preferred embodiment, said condition or disease, preferably said infection, is caused by *Staphylococcus aureus*. In another preferred embodiment, said condition or disease, preferably said infection, is caused *Klebsiella pneumoniae*. In another preferred embodiment, said condition or disease, preferably said infection, is caused *Acinetobacter baumannii*. In another preferred embodiment, said condition or disease, preferably said infection, is caused *P. aeruginosa*. In another preferred embodiment, said condition or disease, preferably said infection, is caused *Enterobacter* spp.

In another preferred embodiment, said condition or disease is caused by bacteria, and wherein said bacteria are Gram-negative bacteria or Gram-positive bacteria. In another preferred embodiment, said condition or disease is caused by Gram-negative bacteria. In another preferred embodiment, said condition or disease is caused by Gram-positive bacteria.

In another preferred embodiment, said condition or disease is caused by Gram-negative bacteria or Gram-positive bacteria selected from *S. pneumoniae, Bacillus* spp, *Listeria monocytogenes, Staphylococcus* spp, lactic acid bacteria, preferably *Lactobacillus plantarum* and *Lactococcus lactis, Streptococcus sobrinus, Streptococcus mutans, Escherichia coli, Pseudomonas aeruginosa*, Entersobacteriaceae, *Salmonella* species, preferably *Salmonella enterica, Salmonella enteritidis* or *Salmonella typhi, Actinobacillus pleuropneumoniae, Proteus mirabilis, Shigella species, Moraxella*, preferably *Moraxella catarrhalis, Helicobacter*, preferably *Helicobacter pylori, Stenotrophomonas*, Bdellovibrio, acetic acid bacteria, *Legionella*, preferably *Legionella pneumophila*, cyanobacteria, spirochaetes, green sulfur, and green non-sulfur bacteria, *Neisseria*, preferably *Neisseria gonorrhoeae* or *Neisseria meningitides, Haemophilus influenza, Enterococcus faecalis, Staphylococcus aureus, Klebsiella pneumoniae, Acinetobacter baumannii, Serratia marcescens, Enterobacter cloacae* and *Enterobacter* spp. In another preferred embodiment, said condition or disease, preferably said infection, is caused by *Haemophilus influenza* or *Serratia marcescens*. In another preferred embodiment, said condition or disease, preferably said infection, is caused by *Haemophilus influenza*. In another preferred embodiment, said condition or disease, preferably said infection, is caused by *Serratia marcescens*.

In another preferred embodiment, said condition or disease, preferably said infection, is caused by at least one ESKAPE pathogen selected from *Enterococcus faecalis, Staphylococcus aureus, Klebsiella pneumoniae, Acinetobacter baumannii, P. aeruginosa* and *Enterobacter* spp., or by *Haemophilus influenza* or *Serratia marcescens*.

In another preferred embodiment, said condition or disease is caused by Gram-negative or Gram-positive bacteria selected from *S. pneumoniae, Bacillus* spp., *Listeria monocytogenes, Staphylococcus* spp, lactic acid bacteria, preferably *Lactobacillus plantarum* and *Lactococcus lactis, Streptococcus sobrinus, Streptococcus mutans, Escherichia coli, Pseudomonas aeruginosa*, Entersobacteriaceae, *Salmonella enterica, Actinobacillus pleuropneumoniae, Proteus mirabilis*.

In another preferred embodiment, said condition or disease is caused by Gram-negative bacteria selected from *Pseudomonas aeruginosa, Escherichia coli*, Entersobacteriaceae, *Salmonella enterica, Actinobacillus pleuropneumoniae*, and *Proteus mirabilis*.

In another very preferred embodiment, said condition or disease is caused by *Pseudomonas aeruginosa*. In another very preferred embodiment, said condition or disease is caused by Gram-negative bacteria, wherein said Gram-negative bacteria is *Pseudomonas aeruginosa*. In another very preferred embodiment, said use is in a method for preventing or reducing bacteria biofilm formation, typically and preferably, on a surface, wherein said bacteria is *Pseudomonas aeruginosa*.

*P. aeruginosa* biofilms act as reservoirs for disease recurrence, impeding complete cure. The biofilm of this opportunistic pathogen is involved in both, chronic infections such as lung infections in cystic fibrosis patients (80% of CF patients are chronically infected by *P. aeruginosa*) and life-threatening recalcitrant hospital-acquired infections including ventilator-associated pneumonia, post-operative wound infections, and skin and soft tissue infections in burn patients. It is also involved in the contamination of medical instruments, devices and tools (Rabin et al. Future Med. Chem. 7 (4) 2015; Tran et al. PLOS Pathogens 10 (11) 2014).

In another preferred embodiment, said condition or disease is caused by Gram-positive bacteria selected from selected from *S. pneumoniae, Bacillus* spp, *Listeria monocytogenes, Staphylococcus* spp, lactic acid bacteria, preferably *Lactobacillus plantarum* and *Lactococcus lactis, Streptococcus sobrinus*, and *Streptococcus mutans*.

In another very preferred embodiment, said condition or disease is caused by *Staphylococcus aureus*. In another very preferred embodiment, said use is in a method for preventing or reducing bacteria biofilm formation, typically and preferably, on a surface, wherein said bacteria is *Staphylococcus aureus*.

*Staphylococcus aureus* biofilms are a major cause for concern in multiple infections and challenge conventional anti-infective approaches, most notably antibiotic therapy. Many clinical isolates of *S. aureus* are either methicillin resistant (MRSA) or multiply drug resistant. Resistance to antibiotic treatments is further amplified by the increased tolerance of biofilm-forming *S. aureus* bacteria to the few antibiotics to which MRSA remains susceptible. Vancomycin is the most commonly administered drug for *S. aureus* biofilm-associated infections, but increased tolerance of biofilms to vancomycin indicated that using combinatorial treatment approaches is necessary.

*S. aureus* biofilms are commonly involved in implant-associated infections (prosthetic orthopedic implants, heart valves, pacemakers and vascular catheters), chronic wounds, osteomyelitis, cystic fibrosis lung infection and endocarditis. For example, cystic fibrosis lung infection is associated with the presence of biofilms and chronic, long-term bacterial persistence with increased mortality. In the case of *S. aureus*, these infections are often caused by MRSA. *S. aureus* is also a major cause of infection of the endocardium or of prosthetic surfaces in the heart, causing infective endocarditis. *S. aureus* endocarditis is increasing with the growing use of surgical procedures involving implantation of prosthetic cardiovascular devices such as prosthetic heart valves, grafts, hemodialysis catheters and pacemakers (Bhattacharya et al. Expert Rev Anti Infect Ther. 13 (12) 2015).

In further preferred embodiments, the method for preventing or reducing biofilm formation or for eradicating or reducing existing biofilm in accordance with the present invention further comprises the administration of a therapeutically effective amount of the inventive composition, the inventive single empty liposomes or the inventive mixture of empty liposomes to a mammal, preferably in a human in need thereof.

For preventing or reducing biofilm formation or for eradicating or reducing existing biofilm, the inventive single empty liposomes or the inventive mixture of empty liposomes can be applied in the form of intravenous, intramuscular, intraperitoneal, or subcutaneous injections. Injection solutions are prepared by standard methods known in the art, for example as suspensions of the liposomes in sterile normal saline. It is also considered to apply the inventive single empty liposomes or the inventive mixture of empty liposomes as aerosol for the treatment of respiratory tract infections, or in a formulation useful for sublingual or buccal application, for intraocular or intravitreal application, as well as for topical application (e.g. eye drops, toothpaste, topical liquid suspensions for the skin or the mouth, and the like). The preparation of such formulations from liposomes such as the empty liposomes of the invention is known in the art. Prophylactic measures based on the inventive single empty liposomes or the inventive mixture of empty liposomes will be helpful in the prevention of biofilm-associated conditions or diseases, for example in the prevention of biofilm development in patients that will undergo, that undergo or have undergone implant surgery, or in patients suffering from chronic infections, or in other settings that favour the development of biofilm-associate conditions or diseases.

In further preferred embodiments, the method for preventing or reducing biofilm formation or for eradicating or reducing existing biofilm, in accordance with the present invention further comprises the administration of a therapeutically effective amount of the inventive composition, the inventive single empty liposomes or the inventive mixture of empty liposomes to a mammal, preferably in a human in need thereof, wherein the inventive composition, the inventive single empty liposomes or the inventive mixture of empty liposomes are administered not in conjunction with any other drug, and thus typically alone, wherein further typically and preferably, the inventive composition, the inventive single empty liposomes or the inventive mixture of empty liposomes are not co-administered at the same time or any time of up to 4 weeks before and after, preferably up to 2 weeks before and after.

In a further preferred embodiment of the present invention, said use is in combination with an antimicrobial agent, wherein preferably said antimicrobial agent is an antibiotic, an antifungal agent, an anti-toxin agent, an anti-virulence agent, an antiseptic, or a combination thereof, and wherein further preferably said antimicrobial agent is an antibiotic.

The present invention also relates to a method for preventing or reducing biofilm formation or for eradicating or reducing existing biofilm, preferably to a method for preventing or reducing biofilm formation, for treating a condition or disease, preferably a bacterial infection, wherein said method comprises administering to a mammal, preferably a human, in need thereof a therapeutically effective amount of the inventive single empty liposome or the inventive mixture of empty liposomes before, after, together or in parallel with a antimicrobial agent, preferably with a standard antibiotic treatment of the bacterial infection.

This preferred aspect and embodiment of the present invention is intended to improve treatment effectiveness, promote planktonic growth and thus removing the additional community level resistance provided by biofilms, facilitate the targeting of pathogens at the cellular level by traditional antibiotics, and also allow antibiotic dose reduction. Moreover, as the inventive single empty liposomes and mixtures of empty liposomes have already been described as a toxin-neutralizer, its action against toxins would, in parallel, disarm bacteria as well as allowing immune defense systems to elaborate appropriate responses against the pathogen.

In further preferred embodiments of the present invention, the method further comprises the administration of a therapeutically effective amount of the inventive composition, the inventive single empty liposomes or the inventive mixture of empty liposomes to a mammal, preferably in a human in need thereof, before, after, together or in parallel with an antimicrobial agent, wherein preferably said antimicrobial agent is an antibiotic, an antifungal agent, an anti-toxin agent, an anti-virulence agent, an antiseptic, or a combination thereof, and wherein further preferably said antimicrobial agent is an antibiotic. In a further preferred embodiment, the method further comprises the administration of a therapeutically effective amount of the inventive composition, the inventive single empty liposomes or the inventive mixture of empty liposomes to a mammal, preferably in a human in need thereof, before, after, together or in parallel with a standard antibiotic treatment and standard of care.

In further preferred embodiments of the present invention, the method further comprises the administration of an effective amount of the inventive composition, the inventive single empty liposomes or the inventive mixture of empty liposomes to an animal, preferably a food animal such as a cow or sheep or pig in need thereof, either not in conjunction with any other drug, and thus typically alone, or before, after, together or in parallel with an antimicrobial agent, wherein preferably said antimicrobial agent is an antibiotic, an antifungal agent, an anti-toxin agent, an anti-virulence agent, an antiseptic, or a combination thereof, and wherein further preferably said antimicrobial agent is an antibiotic. In a further preferred embodiment, the method further comprises the administration of an effective amount of the inventive composition, the inventive single empty liposomes or the inventive mixture of empty liposomes to an animal, preferably a food animal such as a cow or sheep in need thereof, before, after, together or in parallel with a standard antibiotic treatment or administration.

In further preferred embodiments of the present invention, the method further comprises the administration of a therapeutically effective amount of the inventive composition, the inventive single empty liposomes or the inventive mixture of empty liposomes to an animal, preferably a food animal such as a cow or sheep or pig in need thereof, either not in conjunction with any other drug, and thus typically alone, or before, after, together or in parallel with an antimicrobial agent, wherein preferably said antimicrobial agent is an antibiotic, an antifungal agent, an anti-toxin agent, an anti-virulence agent, an antiseptic, or a combination thereof, and wherein further preferably said antimicrobial agent is an antibiotic. In a further preferred embodiment, the method further comprises the administration of a therapeutically effective amount of the inventive composition, the inventive single empty liposomes or the inventive mixture of empty liposomes to an animal, preferably a food animal such as a cow or sheep in need thereof, before, after, together or in parallel with a standard antibiotic treatment.

In further preferred embodiments of the present invention, the method further comprises contacting or coating a therapeutically effective amount of the inventive composition, the inventive single empty liposomes or the inventive mixture of empty liposomes to a surface, preferably a plant surface, either not in conjunction with any other drug, and thus typically alone, or before, after, together or in parallel with an antimicrobial agent, wherein preferably said antimicrobial agent is an antibiotic, an antifungal agent, an anti-toxin agent, an anti-virulence agent, an antiseptic, or a combination thereof, and wherein further preferably said antimicrobial agent is an antibiotic.

It is understood that the empty liposomes as defined above and the mixtures of empty liposomes as defined above may, if desired, be used together or in combination with further compounds, prodrugs or drugs. For example, it is possible to add further compounds, prodrugs or drugs to prepare standard pharmaceutical compositions. It is also considered to add drugs or drug-like compounds, or to add further known or novel liposomes incorporating drugs or drug-like compounds in the liposome interior.

Drugs and prodrugs considered are, in particular, standard antimicrobial or antifungal treatments or anti-toxin or anti-virulence agents which are known to the skilled person in the art. Furthermore, drugs such as antibiotics are, in particular, considered. Such antibiotics are, for example, carbapenems, such as imipenem/cilastatin, meropenem, ertapenem, and doripenem; 1st generation cephalosporins, such as cefadroxil and cefalexin; 2nd generation cephalosporins, such as cefuroxime, cefaclor, and cefprozil; 3rd generation cephalosporins, such as ceftazidime, ceftriaxone, cefixime, cefdinir, cefditoren, cefotaxime, cefpodoxime, and ceftibuten, 4th generation cephalosporins, such as cefepime; 5th generation cephalosporins, such as ceftaroline fosamil and ceftobiprole; glycopeptides, such as vancomycin, teicoplanin, and telavancin; macrolides, such as clarithromycin, azithromycin, dirithromycin, erythromycin, roxithromycin, troleandomycin, telithromycin, spectinomycin, and spiramycin; penicillins, such as amoxicillin, flucloxacillin, oxacillin, carbenicllin, and piperacillin; penicillin combinations, such as amoxicillin/clavulanate, piperacillin/tazobactam, ampicillin/sulbactam, and ticarcillin/clavulanate; quinolones, such as ciprofloxacin (e.g. Aradigm's liposomal ciprofloxacin) and moxifloxacin; drugs against mycobacteria, such as rifampicin (rifampin in US), clofazimine, dapsone, capreomycin, cycloserine, ethambutol, ethionamide, isoniazid, pyrazinamide, rifabutin, rifapentine, and streptomycin; other antibiotics, such as metronidazole, arsphenamine, chloramphenicol, fosfomycin, fusidic acid, linezolid, mupirocin, platensimycin, quinupristin/dalfopristin, rifaximin, thiamphenicol, tigecycline, and tinidazole; aminoglycosides, such as amikacin, gentamicin, kanamycin, neomycin, netilmicin, tobramycin (e.g. Axentis' Fluidosomes™ tobramycin) and paromomycin; sulfonamides, such as mafenide, sulfonamidochrysoidine, sulfacetamide, sulfadiazine, silver sulfadiazine, sulfamethizole, sulfamethoxazole, sulfanilamide, sulfasalazine, sulfisoxazole, trimethoprim, and trimethoprim-sulfamethoxazole (co-trimoxazole, TMP-SMX); tetracyclines, such as demeclocycline, doxycycline, minocycline, oxytetracycline, and tetracycline; lincosamides, such as clindamycin, and lincomycin; and lipopeptides, such as daptomycin.

Other drugs considered are for example anti-inflammatory drugs, including corticosteroids (glucocorticoids), such as hydrocortisone (cortisol), cortisone, prednisone, prednisolone, methylprednisolone, dexamethasone, betamethasone, triamcinolone, beclometasone, fludrocortisone acetate, deoxycorticosterone acetate (DOCA), aldosterone, budesonide, desonide, and fluocinonide; non-steroidal anti-inflammatory drugs, e.g. salicilates, such as aspirin (acetylsalicylic acid), diflunisal, and salsalate; propoinic acid derivatives, such as ibuprofen, dexibuprofen, naproxen, fenoprofen, ketoprofen, dexketoprofen, flurbiprofen, oxaprozin, and loxoprofen; acetic acid derivatives, such as indomethacin, tolmetin, sulindac, etodolac, ketorolac, diclofenac, and nabumetone; enolic acid (oxicam) derivatives, such as piroxicam, meloxicam, tenoxicam, droxicam, lornoxicam, and isoxicam; fenamic acid derivatives (fenamates), such as mefenamic acid, meclofenamic acid, flufenamic acid, and tolfenamic acid; selective COX-2 inhibitors (coxibs), such as Celecoxib; and others, such as licofelone.

Further drugs considered are for example vasopressors and vasoconstrictors, such as vasopressin, oxymetazoline, phenylephrine, propylhexedrine, pseudoephedrine, epinephrine, norepinephrine, dopamine, and antihistamines.

Also considered are other type of drugs, for example paracetamol (pain killer), nystatin, amphotericin B, polyenes, azoles and triazoles, nucleoside analogs, echinocandins, pneumocandins (against fungal infections), bupivacaine (post-surgical pain control), morphine (pain killer), verteporfin (ophthalmological diseases), estradiol (menopausal disturbances), Aganocide® compounds.

In this combination treatment the inventive empty liposomes and liposome mixtures may be considered as adjuvants, and the corresponding method of treatment as adjunct treatment.

In further a preferred embodiment of the present invention, said method is an ex-vivo method, wherein preferably said method comprises contacting a surface, preferably a surface of a medical device, with any one of the inventive composition.

In a further aspect, the present invention provides for a method for preventing or reducing biofilm formation, preferably bacteria biofilm formation, on a surface or for eradicating or reducing existing biofilm on a surface, comprising contacting said surface or existing biofilm with any one of the inventive composition.

In a further aspect, the present invention provides for a method for preventing or reducing biofilm formation, preferably bacteria biofilm formation, on a surface or for eradicating or reducing existing biofilm on a surface, wherein said method comprises coating said surface or existing biofilm with any one of the inventive composition.

In a further aspect, the present invention provides for a method for preventing or reducing biofilm formation, preferably bacteria biofilm formation, on a surface or for eradicating or reducing existing biofilm on a surface, comprising treating said surface or existing biofilm with any one of the inventive composition.

In a further aspect, the present invention provides for an ex-vivo method for preventing or reducing biofilm formation, preferably bacteria biofilm formation, on a surface or for eradicating or reducing existing biofilm on a surface, comprising contacting said surface or existing biofilm with any one of the inventive composition. Thus, said inventive method is not a method for treatment of the human or animal body by therapy.

In a further aspect, the present invention provides for an ex-vivo method for preventing or reducing biofilm formation, preferably bacteria biofilm formation, on a surface or for eradicating or reducing existing biofilm on a surface, wherein said method comprises coating said surface or existing biofilm with any one of the inventive composition.

In a further aspect, the present invention provides for an ex-vivo method for preventing or reducing biofilm formation, preferably bacteria biofilm formation, on a surface or for eradicating or reducing existing biofilm on a surface, comprising treating said surface or existing biofilm with any one of the inventive composition. Thus, said inventive method is not a method for treatment of the human or animal body by therapy.

Methods for coating a surface with a biologically or pharmaceutically active compound or composition are well known in the art. For example, the non-biological surfaces mentioned above, i.e. the surface of a medical device may be coated by blending the inventive compositions into film-forming components, and are made into an anti-biofilm coating which can be used to inhibit biofilm formation on the surface of the medical device. The film-forming components may comprise one or more resin, such as but not limited to, one or more hydrolysable, soluble or insoluble resins. For example, the resins can be one or more of glyptal resin, acrylic resin, chlorinated rubber resin, epoxy resin, silicone resin, polyester resin, polyurethane resin, fluoropolymer resin, and other resins known to the skilled person in the art.

EXAMPLES

Liposomes:
Sphingomyelin (SM; CAS No. 85187 October 6) from egg yolk was purchased from Sigma (S0756), Avanti Polar Lipids (860061) or Lipoid GmbH.

Cholesterol (CHOL; CAS No. 57-88-5) from ovine wool grease was purchased from Sigma (C-8667), Avanti Polar Lipids (70000) or Dishman Netherlands B.V.

It is in accordance with the present invention that sphingomyelin (SM) and cholesterol (CHOL) comprised by or consisted of by the inventive empty liposomes or the inventive mixtures of empty liposomes may be either obtained from natural sources as indicated above or alternatively by way of chemical synthesis.

Liposomes Preparation
Unilamellar sphingomyelin: cholesterol (35:65 molar ratio) and sphingomyelin only (100%) liposomes were prepared using sonication or microfluidization (e.g. high pressure homogenization or according to a hydration, extrusion, and diafiltration process protocol.

Sonication:
The lipids were individually dissolved in chloroform at 1 mg/ml concentrations and stored at −20° C. For the preparation of liposomes the chloroform solutions of individual lipids were mixed in the proportions, as required, to produce routinely 50-500 µl of the final solution. Chloroform was completely evaporated for 20-50 min at 60° C. 50 µl or 100 µl of Tyrode's buffer (140 mM NaCl, 5 mM KCl, 1 mM MgCl$_2$, 10 mM glucose, 10 mM HEPES; pH=7.4) containing 2.5 mM CaCl$_2$) was added to the tubes containing films of dried lipids and vigorously vortexed. The lipid suspensions were incubated for 20-30 min at 45° C. in an Eppendorf thermomixer with vigorous shaking. To produce liposomes, the final lipid suspensions were sonicated 3×5 sec at 6° C. in a Bandelin Sonopuls sonicator at 70% power. The liposomal preparations were left for at least 1 hour at 6° C. before they were used in experiments.

Hydration, Extrusion, and Diafiltration Process Protocol:
In an alternative method, each liposomal formulation was made by the ethanol hydration and extrusion method. Lipids were individually dissolved in ethanol and t-butanol while mixing at elevated temperature (~55° C.). The lipid solution was then added to a PBS Buffer Solution (Sodium Chloride, Monosodium Phosphate, Dihydrate and Disodium Phosphate, Dihydrate dissolved in water for injection while mixing, adjusted to a pH of 7.0-7.4 with either hydrochloric acid (HCl) or sodium hydroxide (NaOH) as required, and filtered through a 0.2 µm filter) while mixing at elevated temperature (~65° C.) for approximately 30 minutes. The ensuing process fluid was then extruded repeatedly through a series of polycarbonate track-etched membranes at elevated pressure and temperature (~65° C.) until the desired particle size was achieved, as measured by dynamic light scattering (example of extruder: LIPEX® Extruders). The ensuing process fluid was then concentrated approximately 2-fold using a 100,000 molecular weight cut-off hollow-fiber cartridge and then diafiltered against approximately 10 volume exchanges of the PBS Buffer Solution to remove the ethanol and t-butanol. At the end of diafiltration, the process fluid was concentrated by approximately 30% to allow subsequent dilution to target lipid concentration. Before dilution, the process fluid was filtered through a 0.2 µm sterilizing-grade filter in order to remove any larger liposomes which could clog the filter during Sterile Filtration. The process fluid was then diluted to a target of 40 mg/mL total lipid with the PBS Buffer Solution. The final formulations were aseptically filtered through two 0.2 µm sterilizing grade filters in series and aseptically filled into glass tubing vials.

The concentration of individual lipids in the liposomes is always given as the weight per weight ratio. In liposomes containing sphingomyelin and cholesterol, the 1:1 (weight per weight) ratio corresponds to 50% (weight per weight) or to 35:65 molar ratio. Specifications are described in Table 1.

TABLE 1

| Specifications liposomes | | | | |
|---|---|---|---|---|
| Mean diameter (nm) | Poly-dispersity index | Zeta potential (mV) | Osmolality (mmol/kg) | pH |
| 40 to 400 | <0.45 | −25 to +2 | 250-400 | 6.5-8.0 |

Example 1

Inhibition of *P. aeruginosa* Multi-Drug Resistant Strain 6077 Biofilm

A preferred inventive mixture of empty liposomes proved to decrease biofilm formation by *Pseudomonas aeruginosa* strain 6077, as revealed by the Crystal violet method. Said preferred inventive mixture of empty liposomes consists of a 1:1 (weight per weight-w/w) mixture of said first empty liposomes and said second liposomes, wherein said first empty liposome is composed of a 1:1 weight ratio (1:1 w/w; 35:65 molar ratio) of sphingomyelin (SM) and cholesterol (CHOL), and said second empty liposomes is composed exclusively of SM.

Method

Briefly, *Pseudomonas aeruginosa* strain 6077 was grown in Trypticase Soy Broth (TSB) and diluted in LB broth containing 2% glucose to a concentration of $1\times10^7$ or of $1\times10^6$ colony forming units (CFU) per mL. One hundred microliters (100 µl) of the diluted inoculum was added to the wells of a 96-well flat-bottomed microtiter plate. Increasing concentrations of preferred inventive mixture of empty liposomes were added in a volume of 100 µL to evaluate inhibition of biofilm formation. Each condition was done in triplicates. Concentrations ranged from 75 µg/mL to 2883 µg/mL. Ciprofloxacin, Gentamicin and Tobramycin were used as controls. The plates were incubated overnight at 37° C. Bacteria were then removed from the wells and the biofilm monolayers were washed. The biofilms were fixed by incubating the plates at 60° C. for 1 hour. Following this incubation the biofilms were stained with a 0.4% crystal violet solution for 5 minutes and then eluted with 70% ethanol. The optical density of the eluted material was measured spectrophotometrically at 600 nm. The positive control consisted in biofilm formation in the absence of the liposomes or control drugs; the negative control consisted in the optical density of wells where no bacterial inoculum had been added (i.e. background noise).

Results

With a bacterial density of $1\times10^7$ cells/well (high bacterial density settings), the preferred inventive mixture of empty liposomes alone (i.e. in the absence of any antibiotics) inhibited biofilm formation as of a concentration of 75 µg/mL, with a maximum inhibition of 72% (FIG. 1). A lower bacterial density of $1\times10^6$ cells/well was also tested in order to circumvent possible "overgrowth" that might have been contributing to the inconsistent ODs. With this lower bacterial density, overall levels of inhibition of biofilm formation by the preferred inventive mixture of empty liposomes were lower (46% inhibition of biofilm formation) but still present in the middle concentrations of the dose response curve (300 to 800 µg/mL). Some biofilm disrupting activity were also observed when the preferred inventive mixture of empty liposomes was applied 8 hours post bacteria inoculation, using the lower bacterial density.

The invention claimed is:

1. A method for eradicating or reducing existing biofilm on a surface in a mammal in need thereof, comprising administering to the mammal, a therapeutically effective amount of a composition consisting of a mixture of empty liposomes, wherein said mixture of empty liposomes consists of
    (a) a first empty liposome consisting of sphingomyelin and 35-60% (weight/weight) cholesterol; and
    (b) a second empty liposome consisting of sphingomyelin,
and wherein said mixture of empty liposomes comprises at least 40% (w/w) of said first and at least 40% (w/w) of said second empty liposome.

2. The method of claim 1, wherein the amount of cholesterol of said empty liposome (a) is 45%-55% (weight per weight).

3. The method of claim 1, wherein said method further comprises the administration of an antimicrobial agent.

4. The method of claim 1, wherein the amount of cholesterol of said empty liposome (a) is about 50% (weight per weight).

5. The method of claim 3, wherein said antimicrobial agent is an antibiotic, an antifungal agent, an anti-toxin agent, an anti-virulence agent, an antiseptic, or a combination thereof.

6. An ex-vivo method for eradicating or reducing existing biofilm on a surface comprising contacting said surface with a composition consisting of a mixture of empty liposomes, wherein said mixture of empty liposomes consists of
    (a) a first empty liposome consisting of sphingomyelin and 35-60% (weight/weight) cholesterol; and
    (b) a second empty liposome consisting of sphingomyelin,
    and wherein said mixture of empty liposomes comprises at least 40% (w/w) of said first empty liposome and at least 40% (w/w) of said second empty liposome.

7. The method of claim 6, wherein said surface is a surface of a medical device.

* * * * *